US008772406B2

(12) United States Patent
Linhardt et al.

(10) Patent No.: US 8,772,406 B2
(45) Date of Patent: Jul. 8, 2014

(54) SYNTHETIC WOOD COMPOSITE

(76) Inventors: Robert J. Linhardt, Albany, NY (US); Jonathan S. Dordick, Schenectady, NY (US); Trevor J. Simmons, San Luis Potosi (MX); Minoru Miyauchi, Guilderland, NY (US); Sang-Hyun Lee, Seoul (KR)

(*) Notice: Subject to any disclaimer, the term of this patent is extended or adjusted under 35 U.S.C. 154(b) by 40 days.

(21) Appl. No.: 12/849,340

(22) Filed: Aug. 3, 2010

(65) Prior Publication Data
US 2011/0190402 A1     Aug. 4, 2011

Related U.S. Application Data

(60) Provisional application No. 61/231,763, filed on Aug. 6, 2009.

(51) Int. Cl.
*C08B 37/00* (2006.01)
*C08G 63/48* (2006.01)
*C08G 63/91* (2006.01)
*C08F 212/04* (2006.01)
*C08K 5/41* (2006.01)

(52) U.S. Cl.
USPC ............. 525/54.3; 524/172; 524/496

(58) Field of Classification Search
USPC ................... 525/54.3; 524/496, 172
See application file for complete search history.

(56) References Cited

U.S. PATENT DOCUMENTS

| | | | |
|---|---|---|---|
| 5,292,813 A | 3/1994 | Patil et al. | |
| 5,558,903 A | 9/1996 | Bhushan et al. | |
| 5,641,466 A | 6/1997 | Ebbesen et al. | |
| 5,753,088 A | 5/1998 | Olk | |
| 5,914,367 A * | 6/1999 | Dordick et al. | 525/54.1 |
| 6,221,487 B1 * | 4/2001 | Luo et al. | 428/364 |
| 6,509,397 B1 * | 1/2003 | Nagele et al. | 524/72 |
| 6,596,033 B1 * | 7/2003 | Luo et al. | 8/115.51 |
| 6,692,827 B2 * | 2/2004 | Luo et al. | 428/369 |
| 6,706,876 B2 * | 3/2004 | Luo et al. | 536/56 |
| 6,765,028 B2 * | 7/2004 | Kadla et al. | 521/61 |
| 6,824,559 B2 | 11/2004 | Michal | |
| 7,709,133 B2 * | 5/2010 | Evans et al. | 429/483 |
| 7,867,359 B2 * | 1/2011 | Medoff | 162/50 |
| 8,182,557 B2 * | 5/2012 | Argyropoulos | 44/605 |
| 2002/0036070 A1 * | 3/2002 | Luo et al. | 162/100 |
| 2002/0037407 A1 * | 3/2002 | Luo et al. | 428/364 |
| 2003/0212157 A1 * | 11/2003 | Kadla et al. | 521/79 |
| 2005/0003224 A1 * | 1/2005 | Haruyama | 428/540 |
| 2005/0288484 A1 * | 12/2005 | Holbrey et al. | 528/480 |
| 2006/0173104 A1 | 8/2006 | Gatenholm et al. | |
| 2007/0006774 A1 | 1/2007 | Rogers et al. | |
| 2008/0041542 A1 * | 2/2008 | Gray et al. | 162/102 |
| 2008/0107698 A1 * | 5/2008 | Luu et al. | 424/404 |
| 2008/0118765 A1 * | 5/2008 | Dorgan et al. | 428/532 |
| 2009/0099300 A1 * | 4/2009 | Gallucci et al. | 524/592 |
| 2009/0192264 A1 * | 7/2009 | Laborie et al. | 525/54.21 |
| 2009/0309072 A1 * | 12/2009 | Hwang et al. | 252/506 |
| 2010/0048829 A1 * | 2/2010 | D'Andola et al. | 525/418 |
| 2010/0112242 A1 * | 5/2010 | Medoff | 428/22 |
| 2010/0222460 A1 * | 9/2010 | Hojo | 524/35 |
| 2010/0319862 A1 * | 12/2010 | Rahman | 162/50 |
| 2011/0251377 A1 * | 10/2011 | Rahman et al. | 530/500 |
| 2011/0285049 A1 * | 11/2011 | Baker et al. | 264/105 |
| 2012/0136097 A1 * | 5/2012 | Berlin | 524/73 |

FOREIGN PATENT DOCUMENTS

| | | |
|---|---|---|
| JP | 11-181105 | 7/1999 |
| WO | 0029672 A1 | 5/2000 |
| WO | 2004/083286 A1 | 9/2004 |
| WO | 2005/098546 A2 | 10/2005 |

OTHER PUBLICATIONS

Zhang et al. (Adv. Mater. 2007, 19, 698-704).*
Rials et al. (Wood and Fiber Science, 21(1) 1989, 80-90).*
Nussbaum (Holz als Roh- and Werkstoff 57, 1999, 419-424).*
Shafizadeh et al. (In Wood Technology: Chemical Aspects; ACS Symposium Series, American Chemical Society, 1977, 57-81).*
Kretschmann et al. (Wood, Kirk-Othmer Encyclopedia of Technology, 2007).*
Aaltonen et al. Carbohydrate Polymers 75 (2009) 125-129, published online Jul. 10, 2008.*
Welton, T., "Room-Temperature Ionic Liquids. Solvents for Synthesis and Catalysis," Chem. Rev., 1999, 99, 2071-2083.
Chiappe, C. and Pieraccini, D., "Ionic Liquids: solvent properties and organic reactivity", J. Phys. Org. Chem., 2005, 18, 275-297.
Novoselov, N. P. et al., "Ionic Liquids and Their Use for the Dissolution of Natural Polymers," Russ. J. Gen. Chem., 2007, 77(8), 1395-1405.
El Seoud, O. A., et al., "Applications of Ionic Liquids in Carbohydrate Chemistry: A Window of Opportunities," American Chem. Society, 2007, 8(9), 2629-2647.
Himmel, M. E., et al., "Biomass Recalcitrance: Engineering Plants and enzymes for Biofuels Production," Science, 2007, 315, 804-807.
Li, C., et al., "Acid in ionic liquid: An effect system for hydrolysis of lignocellulose," Green Chem., 2008, 10(2), 177-182.
Brown, R. M., Jr., "Cellulose Structure and Biosynthesis: What is in Store for the 21st Century," J. Polym. Sci. Part A—Polym. Chem., 2004, 42, 487-495.
Swatloski, R.P., et al., "Dissolution of Cellose with Ionic Liquids", J. Am. Chem. Soc., 2002, 124, 4974-4975.
Fukaya,Y., et al., "Superior Solubility of Polysaccharides in Low Viscosity, Polar, and Halogen-Free 1,3-Dialkylimidazolium Formates", American Chem Society, 2006, 7(12), 3295-3297.
Zhao, H., et al., "Designing enzyme-compatible ionic liquids that can dissolve carbohydrates," Green Chem., 2008, 10, 696-705.
Kosan, B., et al., "Dissoultion and forming of cellulose with ionic liquids," Cellulose, 2008, 15, 59-66.
Lee, S. H., et al., "Ionic Liquid-Mediated Selective Extraction of Lignin from Wood Leading to Enhanced Enzymatic Cellulose Hydrolysis," Biotechnol. Bioengineer., 2009, 102(5), 1368-1376.
Fort, D. A. et al., "Can ionic liquids dissolve wood? Processing and analysis of lignocellulosic materials with 1-n-butyl-3-methylimidazolium chloride," Green Chem., 2007, 9, 63-69.

(Continued)

*Primary Examiner* — Liam J Heincer
(74) *Attorney, Agent, or Firm* — Mahreen Chaudhry Hoda, Esq.; Carolyn S. Elmore, Esq.; Elmore Patent Law Group, P.C.

(57) ABSTRACT

The invention is directed a synthetic wood composite comprising biomimetic macromolecules and methods for the preparation thereof.

34 Claims, 8 Drawing Sheets

(56) References Cited

OTHER PUBLICATIONS

Kilpelainen, I., et al., "Dissolution of Wood in Ionic Liquids," J. Agricul. Food Chem., 2007, 55, 9142-9148.

Gabrielii, I., and Gatenholm, P., "Preparation and Properties of Hydrogels Based on Hemicellulose," J. of Applied Polym. Science, 1998, 69, 1661-1667.

Goksu, E. I., et al., "Production and Characterization of Films from Cotton Stalk Xylan," J. Agric. Food Chem., 2007, 55, 10685-10691.

Tharanathan, R.N., "Biodegradeable films and composite coatings: past, present and future," Trends Food Science Technol., 2003, 14, 71-78.

Yang, C., et al., "Modified carbon nanotube composites with high dielectric constant, low dielectric loss and large energy density," Carbon, 2009, 47, 1096-1101.

Zhao, X., et al., "Spray deposited fluoropolymer/multi-walled carbon nanotube composite films with high dielectric permittivity at low percolation threshold," Carbon, 2009, 47, 561-569.

Minami, et al., "Cellulose Derivatives as Excellent Dispersants for Single-Wall Carbon Nanotubes as Demonstrated by Absorption and Photoluminescene Spectroscopy," Applied Physics Letters, 88:09312-1-09312-3, 2006.

* cited by examiner

SYNTHETIC WOOD COMPOSITE

RELATED APPLICATION

This application claims the benefit of U.S. Provisional Application No. 61/231,763 filed Aug. 6, 2009. The entire teachings of the above application are incorporated herein by reference.

BACKGROUND OF THE INVENTION

Wood-based films and coatings can be used in the several fields including food packaging materials, specialized films, and antibacterial or UV protective coatings due to their low cost, renewability, and biodegradability. The use of cellulose and/or hemicelluloses films is advantageous due to their biodegradability. Cellulose films can be easily made by cellophane process or dissolution procedure using ionic liquids. Hemicellulose films using xylan as the most common hemicellulose source can be obtained with the addition of film-making plasticizer. However, cellulose and hemicelluloses films lack the physicochemical properties required to replace petrochemical-based plastic film.

It would therefore be advantageous to develop a biodegradable synthetic wood film or coating with improved physicochemical properties.

SUMMARY OF THE INVENTION

The present invention is directed to a synthetic wood composite comprising biomimetic macromolecules and methods for the preparation thereof.

In one embodiment, the invention is a composite comprising at least two polymeric macromolecules, wherein at least one macromolecule is lignin and the other macromolecule is selected from the group consisting of cellulose and hemicellulose, or a combination thereof.

In some embodiments, the composite comprises lignin, cellulose and hemicellulose. In other embodiments, the hemicellulose is xylan.

In other aspects the composite further comprises a component selected from the group consisting of an organic or inorganic polymer, a polysaccharide, a protein, a cell, a virus, a pigment and a carbon nanotube.

In an additional embodiment, the composite is a fiber. In yet another embodiment, the composite is an electrospun fiber.

In another aspect, the invention is a method of preparing a composite comprising lignin and a macromolecule selected from the group consisting of cellulose and hemicellulose, or a combination thereof; comprising dissolving the lignin and component selected from cellulose or hemicellulose in an ionic liquid and obtaining the composite.

In some embodiments, the method comprises the steps of:
a. Dissolving the lignin and additional component in an ionic liquid to obtain a solution;
b. Applying the solution to a surface and obtaining a hydrogel; and
c. Drying the hydrogel to obtain the composite.

In another embodiment, the invention is an antimicrobial composition comprising a composite comprising at least two polymeric macromolecules, wherein at least one macromolecule is lignin and the other macromolecule is selected from the group consisting of cellulose and hemicellulose, or a combination thereof. In yet another embodiment, the composite further comprises a polysaccharide. In a further aspect, the composite further comprises an antimicrobial agent.

In an additional aspect, the invention includes a UV protective coating comprising a composite comprising at least two polymeric macromolecules, wherein at least one macromolecule is lignin and the other macromolecule is selected from the group consisting of cellulose and hemicellulose, or a combination thereof.

The invention additionally encompasses a dielectric material comprising a composite comprising at least two polymeric macromolecules, wherein at least one macromolecule is lignin and the other macromolecule is selected from the group consisting of cellulose and hemicellulose, or a combination thereof, wherein the composite further comprises a carbon nanotube.

These and other aspects of the invention, as well as various advantages and utilities, will be more apparent with reference to the drawings and the detailed description of the embodiments of the invention.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
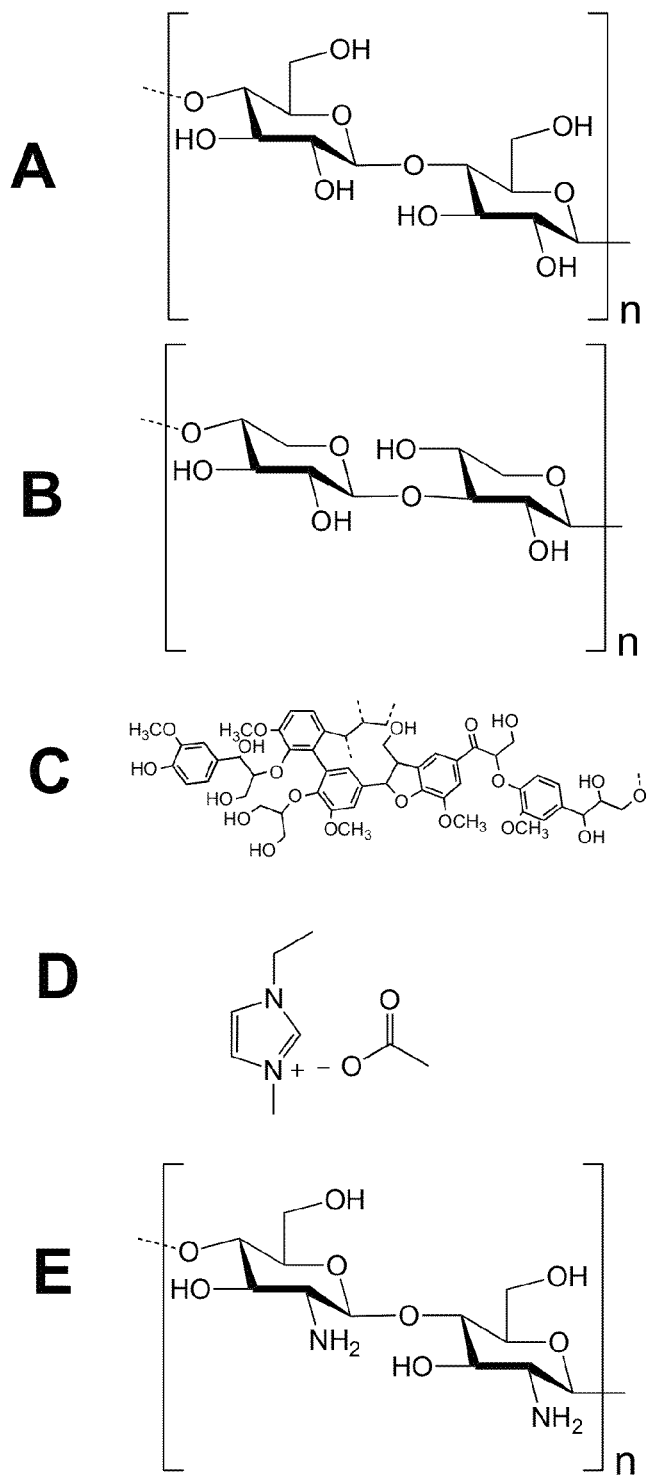
FIGS. 1A to 1E shows the structures of cellulose, xylan, lignin, [Emim][Ac] and chitosan.

A description of preferred embodiments of the invention follows.

The words "a" or "an" are meant to encompass one or more, unless otherwise specified.

The invention is directed to a composite comprising lignin and a polymeric macromolecule selected from the group consisting of cellulose, hemicellulose and a combination thereof and methods for the preparation thereof. As shown in Example 1, a composite comprising lignin, xylan and cellulose had greater tensile strength and had a more uniform, homogenous surface than a film made from cellulose alone.

A composite is a material comprised of at least two constituents, wherein each constituent has different physical or chemical properties.

Cellulose is a linear polysaccharide of D-glucose residues linked by β(1→4)-glycosidic bonds. The term "cellulose" expressly encompasses functionalized or chemically modified cellulose. Functionalized cellulose includes, but is not limited to, acylated, carbanilated and etherified cellulose.

Hemicelluloses are heterogenous, branched polymers of pentoses, hexoses and acetylated sugars. Nonlimiting examples of sugar and/or sugar acid units found in hemicellulose include one or more of the following: pentoses, such as xylose, arabinopyranose and arabinofuranose; hexoses, such as glucose, mannose and galactose; hexuronic acids, such as glucuronic acid, methylglucuronic acid and galacturonic acid; and deoxy-hexoses, such as rhamnose and fucase. The principal, simple sugars that combine to form hemicelluloses are: D-glucose, D-xylose, D-mannose, L-arabinose, D-galactose, D-glucuronic acid and D-galacturonic acid. A hemicellulose can be obtained by chemical and/or enzymatic processes known by those of ordinary skill in the art from a wood source, such as wood pulp, and/or from a non-wood source. Hemicellulose can be obtained from wood pulp from hardwood trees, such as birch, eucalyptus and/or acacia trees. Hemicellulose can also be obtained from wood pulp from softwood trees, such as northern softwood trees and/or southern softwood trees. Nonlimiting examples of non-wood sources of hemicellulose include corn hulls and/or corn brans. In certain embodiments, the hemicellulose is a xylan. The term "hemicellulose" expressly encompasses functionalized or chemically modified cellulose. Functionalized hemicellulose includes, but is not limited to, acylated, carbanilated and etherified hemicellulose.

Lignin is a complex aromatic polymer that is often produced commercially as a product of the paper industry. The physical and chemical properties of lignin can differ depending on the extraction technology and the plant material from which it is extracted. Lignosulfonates (also called lignin sulfonates and sulfite lignins) are products of sulfite pulping. Kraft lignins (also called sulfate lignins) are obtained from the Kraft pulping process. The kraft process is a chemical pulping process where chipped wood is "cooked" or digested in a high temperature broth of sodium hydroxide and sodium sulfide cooking liquor. The term "lignin" as used herein expressly encompasses functionalized or chemically modified cellulose. Functionalized lignins include, but are not limited to, carboxylated and acylated lignin, as well as sulfated lignins and lignins emanating from the kraft process. In addition, unmodified lignin can be used, which is obtained from wood or woody tissue in plants wherein the native structure of the lignin is substantially retained.

The lignin content of the composite can be from about 10 to about 50% (w/w). In one embodiment, the lignin content is from about 20 to about 40% (w/w). In some embodiments, the lignin content is equal to or less than the cellulose content.

The cellulose content of the composite can be from about 20 to about 90% (w/w). In one embodiment, the cellulose content is from about 30 to about 80% (w/w). In another embodiment, the cellulose content is from about 40 to about 60% (w/w).

The hemicellulose content of the composite can be from about 10 to about 50% (w/w). In one embodiment, the hemicelluloses content is from about 20 to about 40% (w/w) hemicellulose.

In some embodiments, the composite comprises cellulose, hemicellulose and lignin. In other embodiments, the composite comprises from about 40 to about 60% (w/w) cellulose, about 20 to about 40% (w/w) hemicellulose and about 10 to about 30% (w/w) lignin. In certain other embodiments, the composite comprises cellulose, lignin and xylan.

The composites of the invention can additionally comprise a component in addition to lignin, cellulose and/or hemicellulose. Examples of additional components that can be made part of the inventive composites include, but are not limited to, organic and inorganic polymers, polysaccharides, peptides, cells, cellular organelles, viruses, pigments, metallic nanowires and carbon nanotubes.

Exemplary polymers include, but are not limited to, polyolefins, polyvinyl chlorides, polyalkylenes, polystyrenes, polyesters, polycarbonates, polyamides, polyvinyl alcohols, polyethylene glycols, polyvinyl acetates, polyethylene oxides, and polyanilines. In one embodiment, the polymer is a polyethylene glycol.

Exemplary polysaccharides are hyaluronic acid, dextran sulfate, chondroitin sulfate, dermatan sulfate, chitin, chitosan, keratin sulfate, heparin, heparan sulfate, and alginate.

An example of a metallic nanowire is a metal oxide nanowire.

Carbon nanotubes are carbon-cage molecule structure, including fullerene, carbon buckyball and carbon nanotube. Carbon nanotubes are divided to carbon nanofibers and carbon nanoparticles based on aggregation. Carbon nanotubes include single walled carbon nanotubes (SWNT), multi-walled carbon nanotubes (MWNT), or a combination thereof. Carbon nanotubes can be prepared in accordance with various processes known in the art (including, for example, U.S. Pat. Nos. 5,753,088, 5,641,466, 5,292,813 and 5,558,903). In some aspects, the invention is directed to a dielectric material comprising composite comprising at least two polymeric macromolecules, wherein at least one macromolecule is lignin and the other macromolecule is selected from the group consisting of cellulose and hemicellulose, or a combination thereof, and further comprising a carbon nanotube. In certain aspects, the carbon nanotube of the dielectric material is a MWNT. In other aspects, the carbon nanotube of the inventive dielectric material is a SWNT.

SWNTs typically have diameters in the range of about 0.5 nanometers (nm) and about 3.5 nm, and lengths usually greater than about 50 nm (B. I. Yakobson and R. E. Smalley, American Scientist, 1997, 324 337; Dresselhaus, et al., Science of Fullerenes and Carbon Nanotubes, 1996, San Diego: Academic Press, Ch. 19). SWNTs are distinguished from each other by a double index (n, m), where n and m are integers that describe how to cut a single strip of hexagonal graphite such that its edges join seamlessly when the strip is wrapped onto the surface of a cylinder. When n=m, the resultant tube is said to be of the "armchair" or (n, n) type, since when the tube is cut perpendicularly to the tube axis, only the sides of the hexagons are exposed and their pattern around the periphery of the tube edge resembles the arm and seat of an armchair repeated n times. When m=0, the resultant tube is said to be of the "zig-zag" or (n, 0) type, since when the tube is cut perpendicular to the tube axis, the edge is a zigzag pattern. Where n≠m and m≠0, the resulting tube has chirality and contains a helical twist to it, the extent of which is dependent upon the chiral angle.

The term "peptide" means an oligomer comprising at least two amino acids. The term "peptide" expressly encompasses proteins. Exemplary proteins include antibodies and enzymes. The term "peptide" is also meant to include proteins or peptide drugs which have been chemically modified. Such chemical modifications include, for example, replacement of an amino acid with a different amino acid or other group and/or addition of a functional group and/or a chemical modifier.

In some embodiments, one or more functional groups can be added to a polymeric macromolecule of the composite. Functional groups can be added to tailor the characteristics of the inventive composite. For example, appropriate functional groups can be added to modify the tensile strength and/or water solubility. One of skill in the art will appreciate that the degree of substitution can be controlled, for example, by changing the reaction time. Exemplary modifications include carboxyl, aldehyde, ketone, ester, ether, amide, thioamide, carbonate, carbamate and anhydride functionalities. In certain embodiments, the macromolecule is acylated, carbanilated or etherified.

In certain aspects, the inventive composite has a thickness of about 10 μm to about 10 mm. In other aspects, the inventive composite has a thickness of at least 1 cm.

In one embodiment, the composite has a tensile strength of at least about 50 MPa. In another embodiment, the composite has a tensile strength of about 70 MPa.

In some other aspects, the composite of the invention has a hydrophobicity such that it has a contact of angle of between about 30 to about 120°.

In other aspects, the composite of the invention is hydrophilic with a contact angle of less than about 45°.

In certain additional aspects, the composite of the invention further comprises a hydrophilic polymer. Non-limiting examples of hydrophilic polymers include polyethylene glycol (PEG), poly(vinyl alcohol), polyvinylpyrrolidone, chitosan, and a combination of any of thereof.

As described below, the composite can be associated with thermal stability. In some aspects, the composite of the invention has a thermal breakdown temperature of about 230° C. or greater.

The invention additionally contemplates a process for the preparation of composites of the invention comprising the step of dissolving the polymeric macromolecules in an ionic liquid to obtain a solution.

Ionic liquids are a class of solvents composed of ionized species in contrast to traditional organic or aqueous solvents which are molecular nonionics. The structure of ionic liquids compared to traditional molecular solvents provides for unique solubilization characteristics. For example, a range of ionic liquids applicable for the dissolution of cellulose are disclosed in U.S. Pat. No. 6,824,559, the contents of which are incorporated by reference herein. Furthermore, ionic liquids have shown good solubility characteristics for monomers or polymers and have been used to reconstitute advanced composites materials, as disclosed in WO 2005/098546, the contents of which are incorporated by reference herein.

Ionic liquids are a class of solvents composed of ionized species in contrast to traditional organic or aqueous solvents which are molecular nonionics. Non-limiting specific examples of useful ionic liquids include materials formed of a cation and an anion. Examples of the cation moiety of ionic liquids are cations from the group consisting of cyclic and acyclic cations. Cyclic cations include pyridinium, imidazolium, and imidazole and acyclic cations include alkyl quaternary ammonium and alkyl quaternary phosphorous cations. Counter anions of the cation moiety are selected from the group consisting of halogen, pseudohalogen and carboxylate. Carboxylates include acetate, citrate, malate, maleate, formate, and oxylate and halogens include chloride, bromide, zinc chloride/choline chloride, 3-methyl-N-butyl-pyridinium chloride and benzyldimethyl(tetradecyl)ammonium chloride. Substituent groups, (i.e. R groups), on the cations can be saturated or unsaturated. Non-limiting examples of compounds which are ionic liquids include, but are not limited to, 1-ethyl-3-methyl imidazolium chloride, 1-ethyl-3-methyl imidazolium acetate, 1-butyl-3-methyl imidazolium chloride, 1-ally-3-methyl imidazolium chloride, zinc chlortide, /choline chloride, 3-methyl-N-butyl-pyridinium chloride, benzyldimethyl(tetradecyl)ammonium chloride and 1-methylimidazolehydrochloride.

The solution obtained from dissolving the polymeric macromolecules will form a hydrogel. In one embodiment, the solution is applied to a surface to obtain a hydrogel. The hydrogel can be washed with water to remove ionic liquid. In some embodiments, the removed ionic liquid can then be reused.

The hydrogel can be dried by appropriate means to obtain the inventive composite.

The composites described herein can be used, for example, in food packaging materials, antimicrobial compositions, automotive interiors, UV protective coatings, dielectric materials, and/or as a part of fabrics and non-woven fabrics.

In one aspect, the invention is directed to a composite described herein that is in the form of a fiber. The fiber can be prepared by any appropriate method including, for example, electrospinning. The composite fibers encompassed by the present invention encompass, for example, nano- and microscale fibers. Fibers of the invention can be used, for example, in the fabrication of non-woven fabrics, artificial leather and/or in filtration methods. In certain aspects, the invention encompasses a non-woven fabric comprised of fibers of the invention. In additional aspects, the invention is directed to a microfiber fabric comprising fibers described herein. Microfiber fabrics and non-woven fabrics can be used, for example, in automotive interiors.

A composite of the invention can also be utilized as a component of a molding or molded part of an automotive interior.

As described below, the inventive composites can be associated with antimicrobial properties. Therefore, in some aspects, the invention is an antimicrobial composition comprising a composite described herein. In additional aspects, the invention is an antimicrobial composition comprising at least two polymeric macromolecules, wherein at least one macromolecule is lignin and the other macromolecule is selected from the group consisting of cellulose and hemicellulose, or a combination thereof, and further comprising a polysaccharide. In certain additional aspects, the polysaccharide is chitosan. In certain additional aspects, the antimicrobial composition is a pharmaceutical composition comprising a therapeutically effective amount of the composite and a pharmaceutically acceptable carrier or excipient. The antimicrobial composition can additionally be used in a method of treating an infection comprising administering to a patient in need of such treatment a therapeutically effective amount of a pharmaceutical composition of the invention. Infections that can be treated by administering a composition described herein include, but are not limited to, bacterial infections, fungal infections, viral infections and protozoal infections. The antimicrobial composition can additionally be used, for example, in a wound-dressing material. In certain other aspects, the wound dressing material comprises a fiber material described herein. In certain additional aspects, the wound dressing material comprises a fiber material fabricated by electrospinning.

In certain additional aspects, the composite or antimicrobial composition of the invention further comprises an antimicrobial agent. Antimicrobial agents include, for example, antibacterial agents, antifungal agents, antiprotozoal agents, sporicidal agents, miticidal agents and antiviral agents. The antimicrobial agent can, for example, be a small molecule or a protein. Non-limiting examples of antimicrobial agents that can be included in the composites of the invention include, but are not limited to, chitosan (as discussed above), nanoscale silver, a silver zeolite, a silver halide, triclosan, an antibiotic (such as rifamycins, macrolides, penicillins, cephalosporins, beta-lactams, aminoglycosides, sulfonamidess, glycopeptides, quinolines, clindamycin, mupirocin, azoles), an antiseptide or disinfectant (such as cationic biguanides, iodine, iodophores, halo-substituted phenolic compounds, triclosan, furans and methenamine), acetic acid, allyl isothiocyanate, benzoic acid, benzoic anhydride, carvacrol, EDTA, eugenol, geraniol, linalool, terpineol, thymol, imazalil, lactic acid, lauric acid, nisin, sodium benzoate, sorbic acid, palmitoleic acid, potassium sorbate, Propionic acid, and sorbic acid anhydride.

"Treating" or "treatment" includes the administration of the compositions, compounds or agents of aspects of the present invention to prevent or delay the onset of the symptoms, complications, or biochemical indicia of a disease, alleviating or ameliorating the symptoms and/or or arresting or inhibiting further development of the disease, condition, or disorder.

A "therapeutically effective amount" is an amount which, alone or in combination with one or more other active agents, can control, decrease, inhibit, ameliorate, prevent or otherwise affect one or more symptoms of a disease or condition to be treated. An "effective amount" is an amount which, alone or in combination with one or more other active agents is sufficient to achieve the indicated objective.

The composites described herein can additionally be associated with the ability to absorb ultraviolet (UV) radiation. Therefore, in some aspects, the invention encompasses a UV protective coating comprising a composite described herein. A UV protective coating is a coating that protects an underlying substrate from UV radiation and the damage resulting therefrom. In certain embodiments, the underlying substrate is a plastic material. In another embodiment, the invention is a method of absorbing UV radiation comprising applying a composite described herein.

The invention is illustrated by the following examples which are not meant to be limiting in any way.

EXAMPLE 1

Preparation of Synthetic Wood Composites Using Ionic Liquids

Synthetic wood composite films containing cellulose, hemicellulose, and lignin, the three major components of natural wood were prepared in a room temperature ionic liquid solvent, 1-ethyl-3-methylimidazolium acetate, [Emim][Ac]. Various synthetic wood composites were obtained by dissolution of individual wood components together with additives, including polyethylene glycol (PEG), chitosan, and multi-walled carbon nanotubes in [Emim][Ac]. The addition of water affords a gel that was dried in either a low humidity environment or under vacuum. Synthetic wood films showed smoother surface textures, higher water resistance, and higher tensile strengths than cellulose films formed by the same methods. Tailor-made synthetic wood composites were also prepared having a variety of desirable properties, including antimicrobial activities, water resistance, conductivity, and a high degree of cohesiveness.

Introduction

Composites are engineered materials made from two or more constituents with different physical or chemical properties.[1] Biopolymer-based composites recently have garnered considerable interest as they can decrease dependency on fossil fuel are often biocompatible, biodegradable, and possess a high degree of functionality. Biopolymers are naturally obtainable macromolecules including polysaccharides, polyphenols, polyesters, polyamides, and proteins.[2] The inherent biodegradability and inexpensive price of these materials make biopolymers particularly promising for developing environmentally friendly materials. However, the preparation of biopolymer-based materials remains a challenge because of the low solubility of many biopolymers in conventional solvents, with the exception of water. Therefore, there is a strong interest in devising new, non-aqueous solvents for the dissolution of biopolymers to prepare biopolymer-based composite materials.

Ionic liquids (ILs) are organic salts that typically melt below 100° C. Interest in ILs stems from their potential application as 'green solvents' because of their non-volatile character and their thermal stability.[3] These desirable properties make ILs attractive alternatives to volatile and often flammable organic solvents for use in chemical processes. ILs exhibit excellent solvent characteristics including the ability to dissolve polar and nonpolar organic, inorganic, and polymeric compounds.[4,5] ILs have recently been used to dissolve and reconstitute biopolymers that are insoluble in most conventional organic solvents.[6,7]

Lignocellulosic biomass, such as agricultural residues, forestry wastes, waste paper, and energy crops has long been recognized for their potential value as sustainable sources of biopolymer composites.[8,9] Lignocellulose consists of three major biopolymers—cellulose, hemicellulose, and lignin—all of which have distinct chemical, physical, and structural properties. Cellulose, a linear polysaccharide of D-glucose residues linked by β-(1→4)-glycosidic bonds (FIG. 1A), is the most abundant renewable biopolymer on earth.[10] It has excellent thermal and mechanical properties. Hemicelluloses are heterogeneous, branched polymers of pentoses, hexoses, and acetylated sugars, with xylans (FIG. 1B) being the most plentiful of the hemicelluloses.[11] Lignin is an aromatic network polymer composed of phenylpropanoid units (FIG. 1C) and represents the "glue" that binds cellulose and hemicellulose.[12]

The use of 1-alkyl-3-methylimidazolium salts as solvents for cellulose was first reported by the Rogers group.[13] They tested the ability of ILs containing the 1-butyl-3-methylimidazolium ([Bmim]) cation with various anions to dissolve cellulose and the most effective anion was found to be the chloride. Cellulose could be dissolved at 25 wt % in [Bmim][Cl] assisted by microwave irradiation, and the dissolved cellulose can be reconstituted by the addition of an antisolvent such as water, ethanol, or acetone. These results have opened up new paths for commercially relevant routes to homogeneous cellulose chemistry for the preparation of various unmodified cellulose composites. Recently, acetate, formate, methyl phosphate, and dicyanamide counter anions of 1-alkyl-3-methylimidazolium salts were reported as good ILs for cellulose dissolution.[14-16] Among the room temperature ILs with low viscosity and toxicity suitable for cellulose dissolution are 1-ethyl-3-methylimidazolium acetate ([Emim][Ac]) (FIG. 1D) and formates of allylimidazolium-based ILs. Recently, our laboratory investigated the solubilities of kraft lignin in various ILs.[17] The highest lignin solubility was obtained using [Mmim][MeSO$_4$] and [Bmim][CF$_3$SO$_3$]. ILs containing the [Cl] anion also showed high solubility (>100 g/kg).

Several groups have reported the full dissolution of woods in ILs.[18,19] By dissolving wood in ILs, solutions were obtained that could be used to analyze the biopolymer composition of woods, Furthermore, these wood components could be functionalized with acetyl, benzoyl, and carbonyl groups. To date, however, the reconstitution of wood, having selected and defined ratios of cellulose, hemicellulose, and lignin, together with additives inducing special properties from fully dissolved solutions in ILs, has not been reported. The current study reports the use of wood component solutions in ILs, which contain varying amounts of cellulose, hemicellulose, and lignin, to fabricate wood films and wood coating composites.

RESULTS AND DISCUSSION

Preparation of Synthetic Wood Film

Figure 2A:
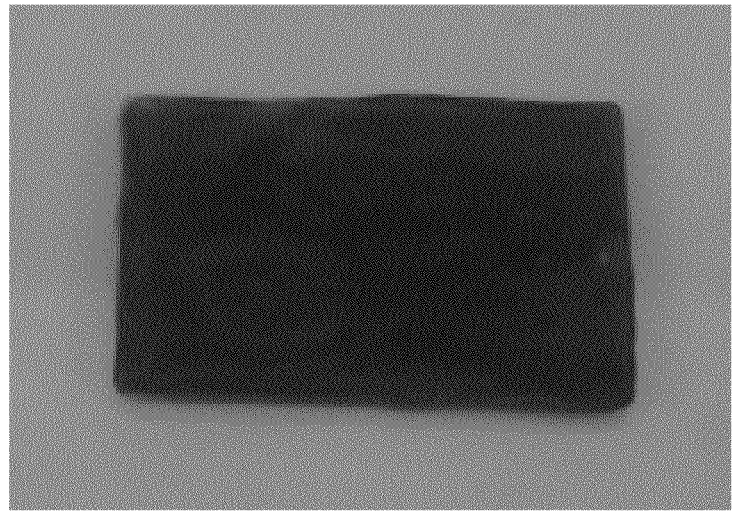
FIG. 2 shows synthetic wood as a hydrogel (A), film (B) and coating (C).
Figure 2B:
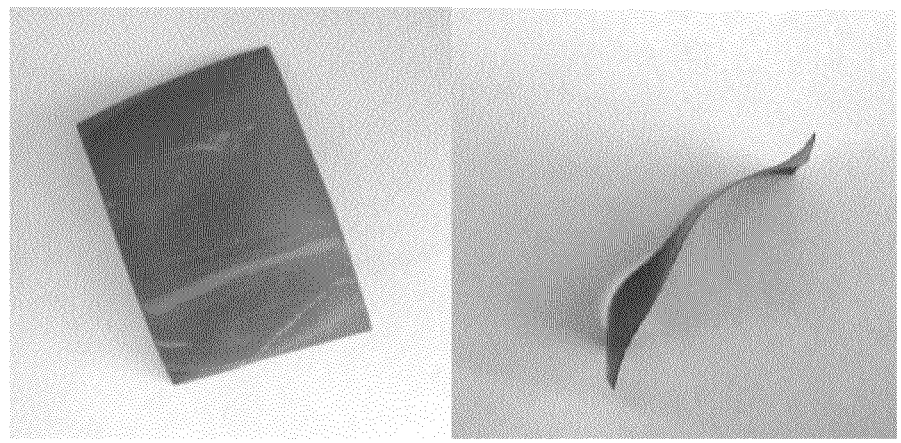
Figure 2C:
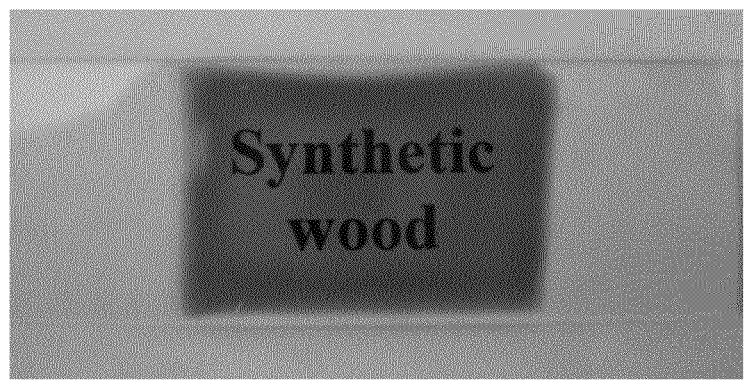

A synthetic wood solution, consisting of 5% (w/w or w/v) cellulose fiber, 3% (w/w) hemicellulose (xylan from birchwood) and 2% (w/w) kraft lignin, was prepared in [Emim][Ac] to mimic a real wood sample. [Emim][Ac] was selected as an excellent solvent for wood components because of the solubility of each wood component in this IL. Cellulose and lignin are soluble in [Emim][Ac] at 90° C. at concentrations >200 and >300 g/kg, respectively.[17] After 3 h of incubation at 90° C., all three wood components dissolved in [Emim][Ac], affording a completely clear solution. Following warm-up, and after washing with water to remove [Emim][Ac], a synthetic wood hydrogel was formed (FIG. 2A), which upon drying for 3 h, afforded a transparent and flexible synthetic wood film that could be easily recovered by peeling if from the glass slide (FIG. 2B). When the synthetic wood film was dried for 1 day in the desiccator, it bonded tightly to the glass slide forming a synthetic wood coating (FIG. 2C) that was water immiscible and could not be easily removed from the glass surface.

Effect of Component Ratios

Figure 3:
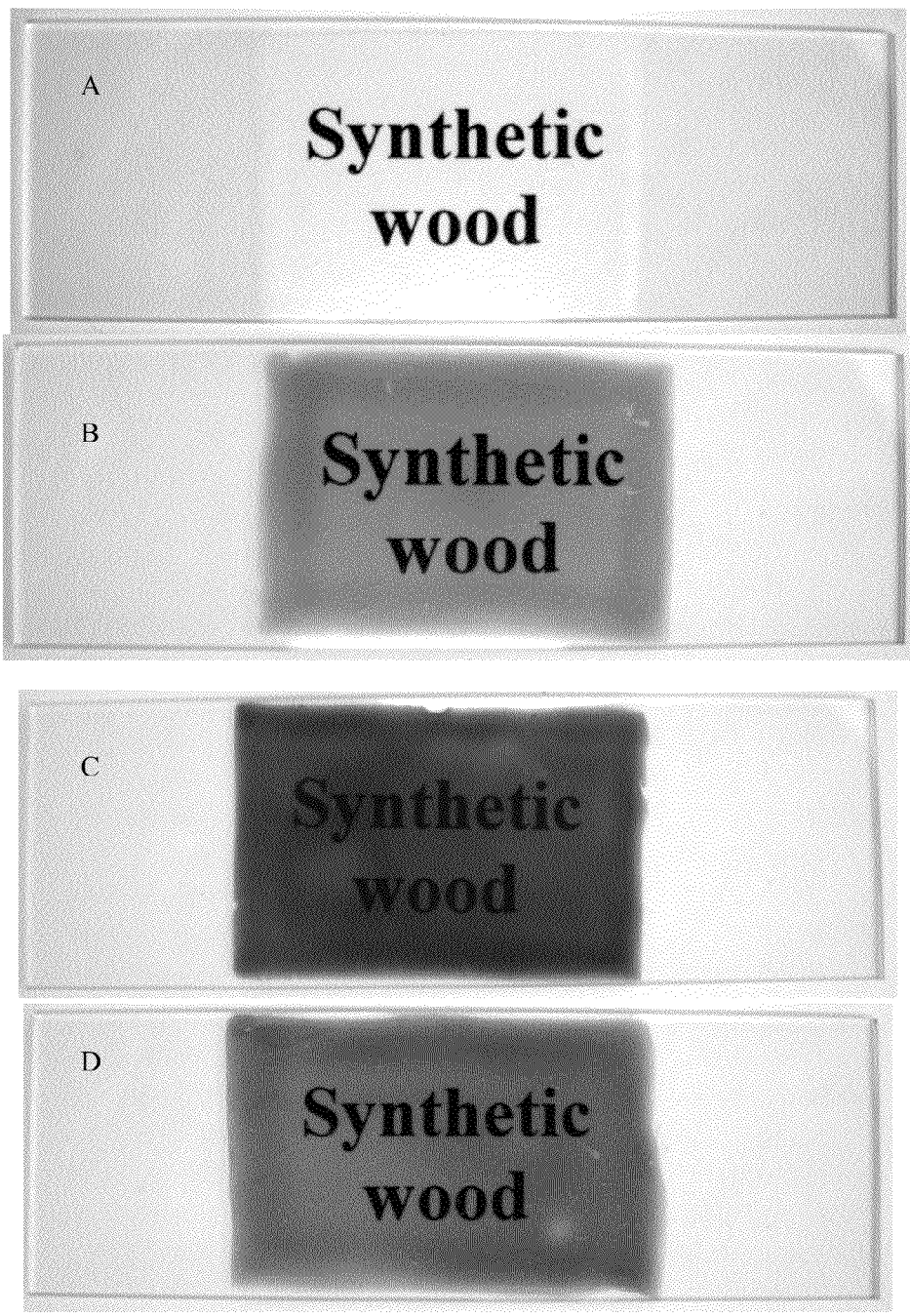
FIG. 3 shows cellulose films (A) cellulose only, (B) cellulose/lignin (5/2, wt. % in [Emim][Ac]), (C) cellulose/lignin (5/5, wt % in [Emim][Ac]) and (D) cellulose/xylan/lignin (5/3/2 wt. % in [Emim][Ac]).
Figure 4A:
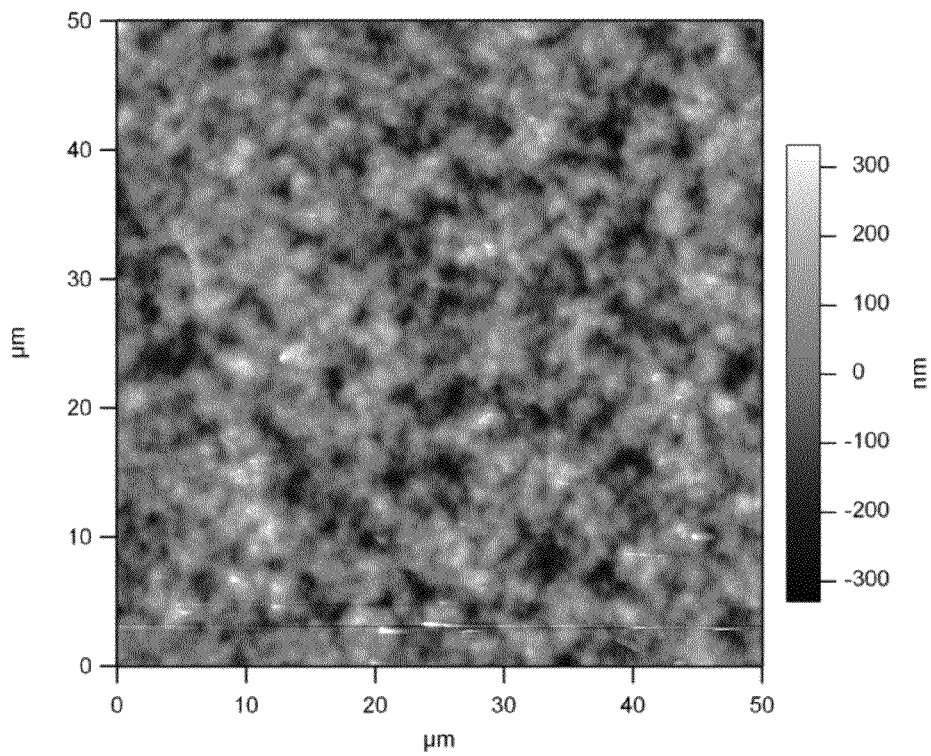
FIG. 4 shows AFM images of the surface of synthetic wood films. (A) cellulose only, (B) cellulose/lignin (5/5, wt. % in [Emim][Ac]) and (C) cellulose/xylan/lignin (5/3/2, wt % in [Emim][Ac]).

A variety of synthetic wood coatings were prepared having differing ratios of cellulose, xylan, and lignin (FIG. 3). Pure cellulose films had been previously prepared by the Roger's group through the dissolution of cellulose in [Bmim][Cl] followed by the reconstitution of cellulose with water.[13] Along these lines, we found that such pure cellulose films could also be easily prepared using [Emim][Ac]. However, these cellulose films were brittle and had rough surfaces (FIG. 4A). Cellulose/lignin composite films with lignin contents reaching as high as that of cellulose were then conveniently prepared by dissolving cellulose together with lignin in [Emim][Ac], washing away the IL with water, and drying. The color of cellulose/lignin composite was light yellow to dark brown, becoming darker with increasing lignin content. However, the cellulose/lignin film becomes very brittle at high lignin contents. Lignin or xylan only films could not be prepared by dissolution in [Emim][Ac] and reconstitution with water. Film formation of pure birch wood xylan requires the addition of a plasticizer such as chitosan and gluten.[20] Recently, Goksu, et al.[21] reported xylan film formation containing a small amount of lignin. We were able to prepare a crack free xylan film from 8-14% xylan solution in water containing >1% lignin (w/w, lignin/xylan). However, the resulting xylan/lignin films showed high water solubility (>99%) and a much lower tensile strength than previously prepared cellulose films.

Potential applications of films for biodegradable packaging materials require high water resistance and good tensile strength. For these reasons, synthetic wood solutions containing cellulose, xylan, and lignin (5:3:2) in [Emim][Ac], were used to obtain films and coating with more optimal properties. Synthetic wood solutions in [Emim][Ac] gave improved film forming properties when compared with cellulose or cellulose/lignin solutions in [Emim][Ac]. The tensile strength of the cellulose and synthetic wood films were 74.4 and 87.8 MPa, respectively. The tensile strength of synthetic wood film is substantially higher than the 1 MPa reported for cellulose or xylan films,[21] and also higher the 15-60 MPa values reported for functionalized celluloses.[22] The high tensile strength of the synthetic wood film appears to result from the presence of lignin, despite the absence of a covalent chemical bond between the cellulose and the lignin. Lignin instead appears to act as a filler of internal structured spaces within the cellulose fibers of the film.

Figure 4B:
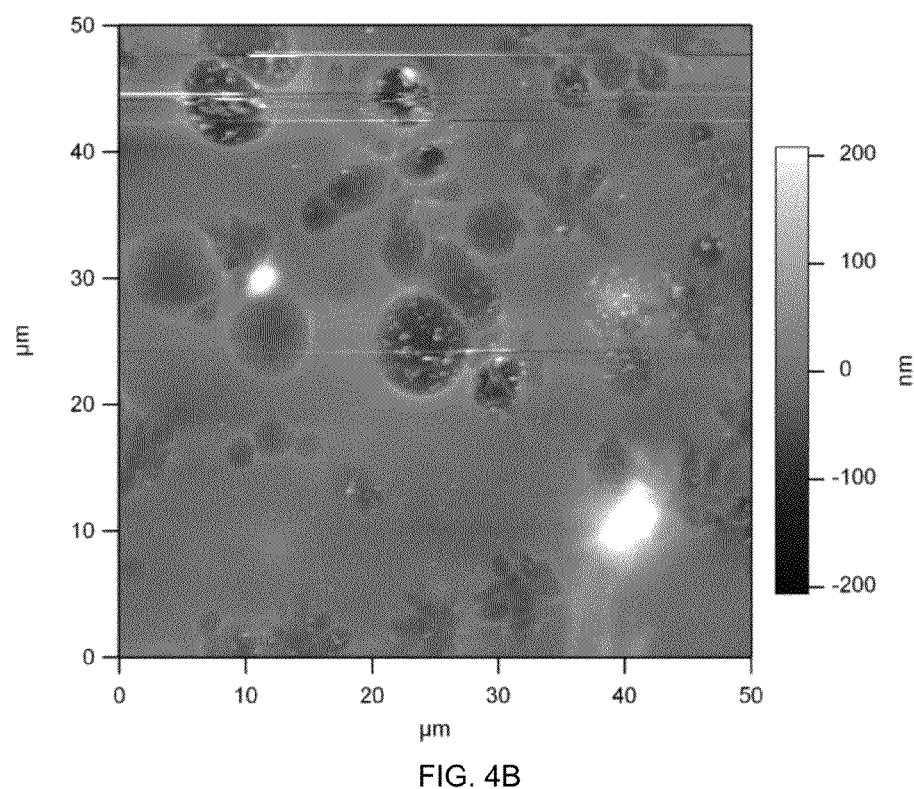
Figure 4C:
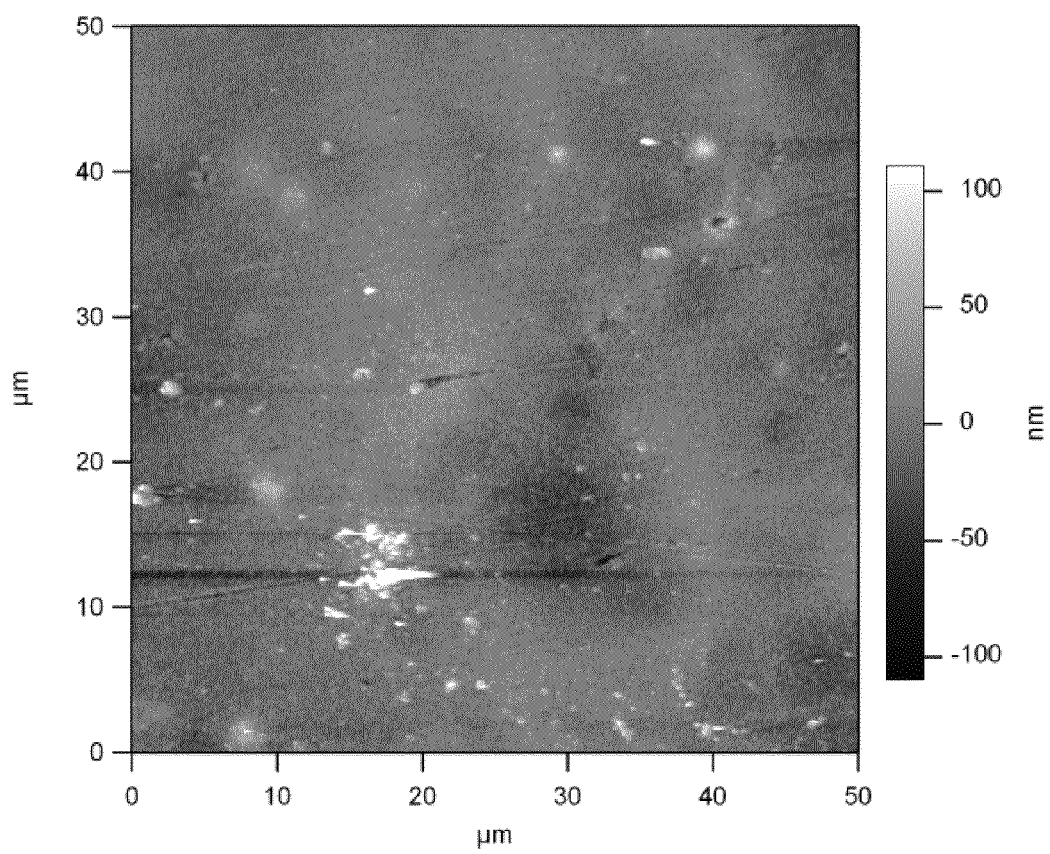
Figure 5A:
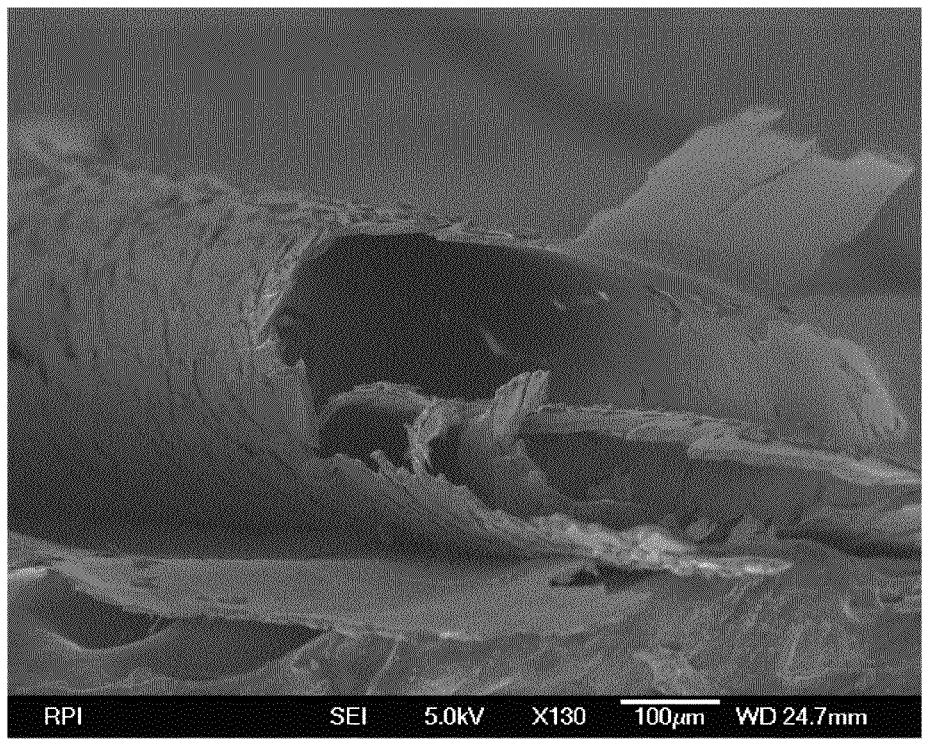
FIG. 5 shows SEM analysis of synthetic woods prepared from [Emim][Ac]) containing (A) 5% cellulose, 0% xylan and 0% lignin, (B) 5% cellulose, 0% xylan and 5% lignin and (C) 5% cellulose, 3% xylan and 2% lignin.
Figure 5B:
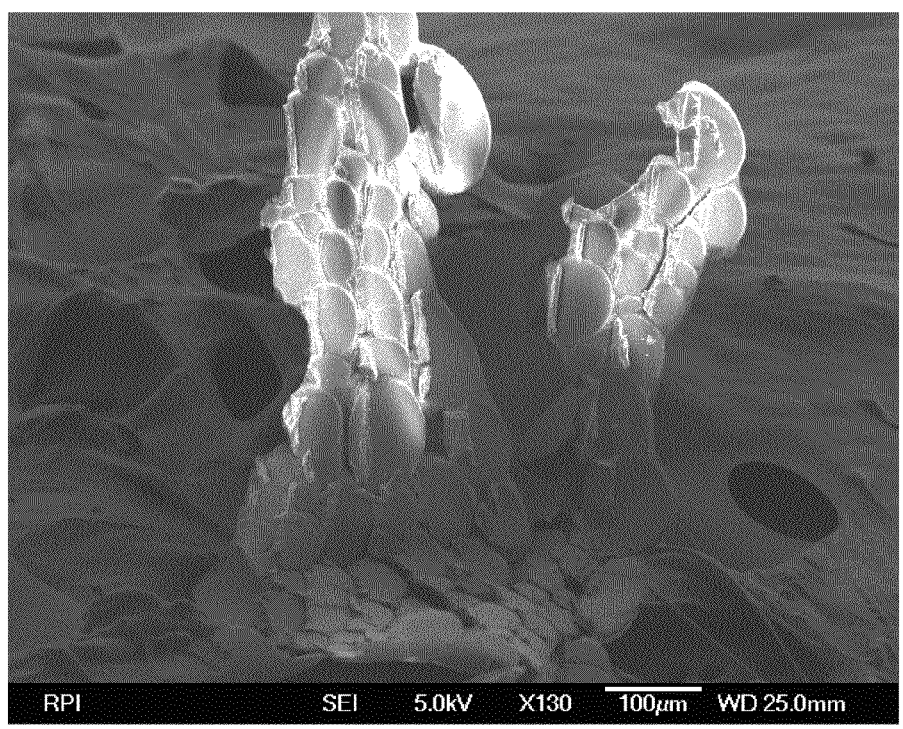
Figure 5C:
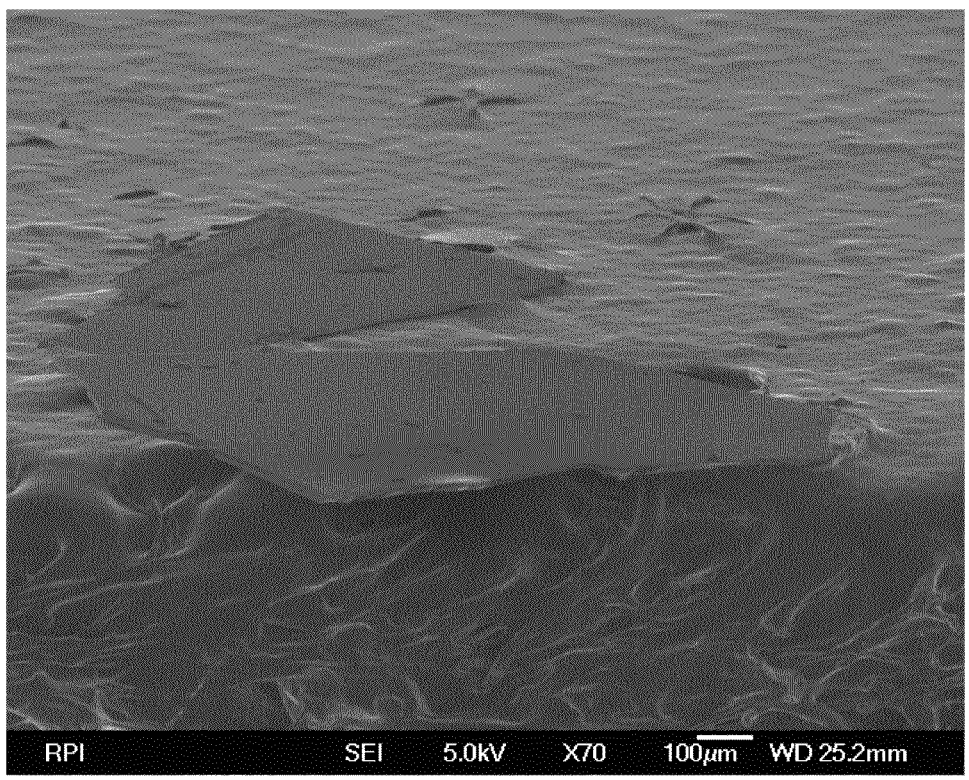

AFM images show that the outer surface of cellulose film (FIG. 4A) has a much rougher surface than the cellulose/xylan/lignin film (FIG. 4C). Cellulose/lignin film (FIG. 4B) afforded a surface that was not uniform. This surface heterogeneity may explain why the cellulose/lignin films become brittle with increasing lignin content. SEM was also used to image cellulose, a cellulose/lignan and a cellulose/xylan/lignan films (FIG. 5). The brittleness of the cellulose only film was readily apparent from its fragmented surface. The cellulose/lignan film gave a surface made of scales while the cellulose/xylan/lignan film had a relatively smooth surface.

Synthetic Wood Composite Films

Figure 6:
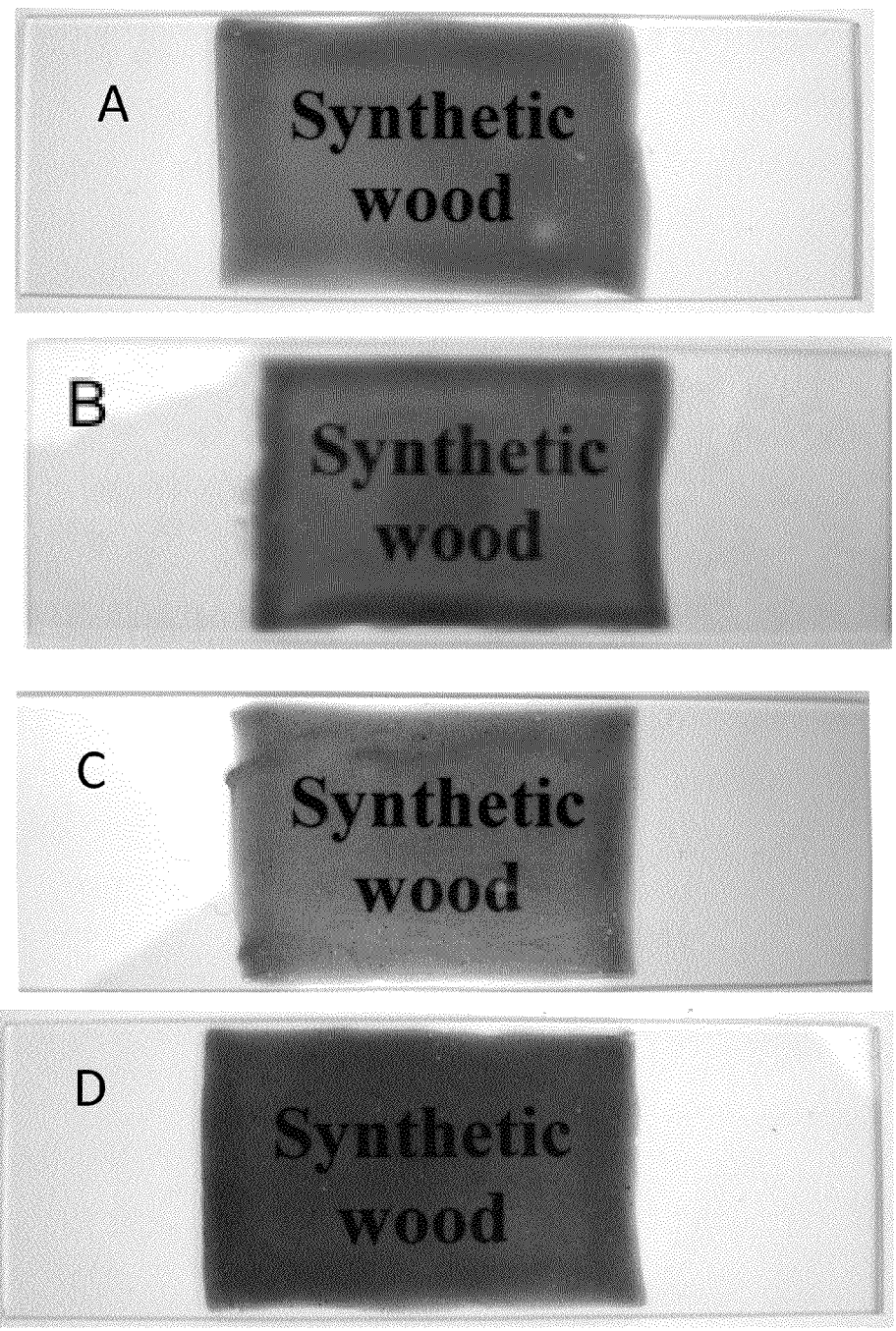
FIG. 6 shows synthetic wood coatings with property altering additives. (A) cellulose/xylan/lignin/PEG (5/3/2/5, wt. % in [Emim][Ac]), (B) cellulose/xylan/lignin/chitosan (5/3/2/0.5, wt. % in [Emim][Ac]), (C) cellulose/xylan/lignin/MWNTs (5/3/2/0.025, wt. % in [Emim][Ac]), and (D) cellulose/xylan/lignin/MWNTs (5/3/2/0.01, wt. % in [Emim][Ac]).

The major reason for using ILs to prepare biopolymer composites is the excellent solvating power of ILs, which can be exploited in the generation of hybrid composites containing both natural and unnatural components. To that end, various synthetic wood/polymer or nanoparticle composites were prepared by dissolving wood components and polymers in [Emim][Ac] followed by reconstitution with water. Synthetic wood (cellulose/xylan/lignin, 5/3/2, wt %)/polymer (5% PEG (MW 400) and 0.5% chitosan (FIG. 1E)) composites were prepared (FIG. 4). After 3 h at 90° C. all of the components dissolved to afford a clear solution that was spin-coated on the glass slide. A transparent and thin film of synthetic wood/polymer composite was obtained after washing with water and drying. The surface of synthetic wood/PEG composite film (FIG. 6A) was stickier and more hydrophilic than the synthetic wood film. The surface of the synthetic wood/chitosan composite film (FIG. 6B) showed an antibacterial effect when challenged with *Staphylococcus aureus*, affording 96% bacterial resistance compared to an identical surface not containing chitosan, a known antibacterial polymer. Synthetic wood/multi-walled nanotube (MWNT) composites were next prepared by using a mixture of synthetic wood solution and dispersed MWNTs. The mixture of MWNT and synthetic wood in [Emim][Ac] (cellulose/xylan/lignin/MTNTs, 5/3/2/0.025 or 0.1 wt. %) was film casted on the glass slide. The resulting synthetic wood/MWNT film was dark and transparent, indicating that the MWNTs were well dispersed (FIG. 6C).

The synthetic wood material prepared with even a high loading (5% wt.) of MWNTs maintained a very high resistance, suggesting that it would make a suitable candidate for a flexible high dielectric insulator composite. High dielectric constant (κ) polymer composites are gaining increasing interest in the field of materials science. Polymer composites containing MWNTs can have exceptionally high dielectric constant values.[23,24] When the MWNT network approaches the percolation threshold for conduction but does not reach it, the values of the dielectric constant are substantially improved. This opens up the possibility of controlled formation of high and low dielectric materials. An example of such an application is in the functional components of batteries and supercapacitors.[25]

EXPERIMENTAL

Reagents

Cellulose solution in [Emim][Ac] (CELLIONIC, degree of polymerization ~680), xylan from birch wood (xylose residues >90% by high performance anion exchange (HPAE) chromatography), [Emim][Ac], PEG (MW 400), and chitosan from crab shells (MW 150,000) were obtained from Sigma-Aldrich (St. Louis, Mo.). Indulin AT, a purified softwood kraft lignin from pine, was generously provided by MeadWestvaco (Charleston, S.C.).

Preparation of Synthetic Wood Solutions in [Emim][Ac]

Xylan (0.3 g) and lignin (0.2 g) were mixed with CELLIONIC (10 g containing 0.5 g cellulose) in a 100 mL round bottom flask. The flask was heated with stirring at 90° C. for 3 h. The resulting dissolved synthetic wood solution (5% cellulose, 3% xylan, and 2% lignin all (wt %)) was used alone or in combination with additives (5% (w/w) PEG or 0.5% (w/w) chitosan) at 90° C. with stirring for 2 h to prepare synthetic wood/polymer composites. Synthetic wood/ MWNT composites were prepared by first using a mortar and pestle to grind 10 mg MWNTs for 20 min in 1 g [Emim][Ac] to disperse the MWNTs. The MWNTs remained dispersed for over 1 month in [Emim][Ac]. The dispersed MWNTs were next mixed with synthetic wood solution (cellulose/ xylan/lignin, 5/3/2, wt %).

Preparation of Synthetic Wood Composites Film and Coating

Synthetic wood solutions (with and without additives) were spin-coated on glass slides. The speed of the spin-coater was increased in steps from 500 rpm to 2500 rpm over 3 min. Coated synthetic wood solution was maintained at room temperature for 10 min and then gently washed with water for 10 min to remove [Emim][Ac]. The synthetic wood hydrogel obtained was dried in a desiccator. After drying for 3 h, a flexible synthetic wood film was obtained that could be easily peeled off from the glass slide. After longer drying periods of 1 day or more, the synthetic wood film tightly attached to the glass slide and could not be easily removed. Thus, all free films tested in the current study were dried for 3 h.

Tensile Strength Test

The tensile strength properties were determined from cast films peeled off and dried for an additional 24 h under vacuum. A Lloyd Material Testing Machine (Lloyd Instrument Ltd.) was used for these measurements. Tensile strength was calculated by dividing the peak load by the initial cross-sectional area of the specimen.

Resistance Measurements

A True RMS MultiMeter (Model Number 22-816) obtained from Extech Instruments (Waltham, Mass.) was used to test the resistance of the MWNT-synthetic wood composite. The two electrodes were inserted at different positions into the composite and resistance was measured.

Antimicrobial Activity

*Staphylococcus aureus* was grown in culture and re-suspended in distilled water at a concentration of $10^4$ CFU per mL. Then 0.1 ml of the cell suspension was spread on a LB agar plate. After drying for 30 min, synthetic wood control and synthetic wood chitosan composite were placed on the surface of separate agar plates and incubated at 37° C. for 48 h. The difference in the antibacterial efficacy of the synthetic wood chitosan composite and synthetic wood were compared by visually examining the agar plates under a UVA lamp.

Conclusions

In this work, synthetic wood composite films were prepared consisting of cellulose, xylan, and lignin, the three major components of lignocellulosic biomass. These films were spin coated from [Emim][Ac] and reconstituted with water and dried. Synthetic wood films had improved physicochemical properties compared to cellulose, xylan, and lignin films. The advantages of synthetic wood composites include low production cost by using renewable biomaterials, reduced biodegradability compared with cellulose composites because of the presence of lignin, greater water resistance, and potential for modification and functionalization. Tailor-made synthetic wood films can be obtained simply by changing component ratios of synthetic wood solution in [Emim][Ac]. By including additives in synthetic wood composites a wide variety of materials can be prepared having special properties, such as high tensile strength, conductivity, and antimicrobial properties. Film color might also represent an important property if the film were to be used for the packaging of light-sensitive materials.

REFERENCES

1. I. Šimkovic, *Carbohydr. Polym.*, 2008, 74, 759.
2. S. H. Lee, M. Miyauchi, J. S. Dordick and R. J. Linhardt, ACS Symposium Series Ionic liquids application: Pharmaceutical, Therapeutics, and Biotechnology, in press, 2009.
3. R. A. Sheldon, R. M. Lau, M. J. Sorgedrager and F. van Rantwijk, *Green Chem.*, 2002, 4, 147.
4. T. Welton, *Chem. Rev.*, 1999, 99, 2071.
5. C. Chiappe and D. Pieraccini, *Phys. Org. Chem.*, 2005, 18, 275.
6. N. P. Novoselov, E. S. Sashina, O. G. Kuz'mina and S. V. Troshenkova, *Russ. J. Gen. Chem.*, 2007, 77, 1395.
7. O. A. El Seoud, A. Koschella, L. C. Fidale, S. Dorn and T. Heinze, *Biomacromolec.*, 2007, 8, 2629.
8. M. E. Himmel, S.-Y. Ding, D. K. Johnson, W. S. Andey, M. R. Nimlos, J. W. Brady and T. D. Foust, *Science*, 2007, 315, 804.
9. C. Li, Q. Wang and Z. K. Zhao, *Green Chem.*, 2008, 10, 177.
10. R. M. Brown, *J. Polym. Sci. Part A—Polym. Chem.*, 2004, 42, 487.
11. B. C. Saha, *Industr. Microbiol. Biotechnol.*, 2003, 30, 279.
12. R. P. Chandra, R. Bura, W. E. Mabee, A. Berlin, B. Pan and J. N. Saddler, Biofuels Book Series: Advances in Biochemical Engineering/Biotechnology, 2007, 108, 67.
13. R. P. Swatloski, S. K. Spear, J. D. Holbrey and R. D. Rogers, *J. Am. Chem. Soc.*, 2002, 124, 4974.
14. Y. Fukaya, A. Sugimoto and H. Ohno, *Biomacromolec.*, 2006, 7, 3295.
15. H. Zhao, B. A. Baker, Z. Y. Song, O. Olubajo, T. Crittle and D. Peters, *Green Chem.*, 2008, 10, 696.
16. B. Kosan, C. Michels and F. Meister, *Cellulose*, 2008, 15, 59.
17. S. H. Lee, T. V. Doherty, R. J. Linhardt and J. S. Dordick, *Biotechnol. Bioengineer.*, 2009, 102, 1368.
18. D. A. Fort, R. C. Remsing, R. P. Swatloski, P. Moyna, G. Moyna and R. D. Rogers, *Green Chem.*, 2007, 9, 63.
19. I. Kilpeläinen, H. Xie, A. King, M. Granstrom, S. Heikkinen and D. S. Agrgyropoulos, *Agricul. Food Chem.*, 2007 55, 9142.
20. I. Gabrielii, and P. Gatenholm, *Appl. Polym. Science*, 1998, 69, 1661.

21. E. I. Goksu, H. Karamanlioglu, U. Bakir, L. Yilmaz and U. Yilmazer, *Agricult. Food Chem.*, 2007, 55, 10685.
22. R. N. Tharanathan, *Trends Food Science Technol.*, 2003, 14, 71.
23. C. Yang, Y. Lin, C. W. Nan, *Carbon*, 2009, 47, 1096.
24. X. Zhao, A. A. Koos, B. T. T. Chu, C. Johnston, N. Grobert, P. S. Grant, *Carbon*, 2009, 47, 561.
25. V. L Pushparaj, S. M. Manikoth, A. Kumar, S. Murugesan, L. Ci, R. Vajtai, R. J. Linhardt, O, Nalamasu, P. M. Ajayan, *Proc. Nat. Acad. Sci. USA* 2007, 104, 13574.

While this invention has been particularly shown and described with references to preferred embodiments thereof, it will be understood by those skilled in the art that various changes in form and details may be made therein without departing from the scope of the invention encompassed by the appended claims.

What is claimed is:

1. A composite comprising lignin, cellulose and hemicellulose, wherein the cellulose content is about 40 to about 60% (w/w), the hemicellulose content is about 20 to about 40% (w/w), and the lignin content is about 10 to about 30% (w/w), wherein the lignin is selected from a kraft lignin or a lignosulfonate, wherein the hemicellulose is xylan, and wherein the composite is transparent.

2. The composite of claim 1 comprising about 50% (w/w) cellulose, about 30% (w/w) hemicellulose and about 20% lignin.

3. The composite of claim 1, further comprising a component selected from the group consisting of organic and inorganic polymers, polysaccharides, peptides, cells, viruses, pigments and carbon nanotubes.

4. The composite of claim 3, wherein the polymer is polyethylene glycol.

5. The composite of claim 4 comprising polyethylene glycol 400.

6. The composite of claim 4 comprising polyethylene glycol in an amount between about 10 to about 40% (w/w).

7. The composite of claim 4, wherein the carbon nanotube is a multi-walled nanotube (MWNT).

8. The composite of claim 3 comprising lignin, cellulose, hemicellulose and polyethylene glycol.

9. The composite of claim 3, wherein the composite comprises a carbon nanotube.

10. The composite of claim 9, wherein the carbon nanotube is present in an amount from about 10 to about 30% (w/w).

11. The composite of claim 3, wherein the polysaccharide is chitosan.

12. The composite of claim 1, wherein the lignin, cellulose, hemicellulose, or a combination thereof, is functionalized.

13. The composite of claim 12, wherein the lignin, cellulose, hemicellulose, or a combination thereof, is acylated, carbanilated or etherified.

14. The composite of claim 1 having a thickness of about 10 μm to about 10 mm.

15. The composite of claim 14 having a tensile strength of at least about 70 MPa.

16. The composite of claim 1 having a tensile strength of at least about 50 MPa.

17. The composite of claim 1, wherein the composite is a fiber.

18. The composite of claim 1, wherein the composite has a contact angle of less than about 45°.

19. The composite of claim 1, wherein the composite has a thermal breakdown temperature of about 230° C. or greater.

20. The composite of claim 1, wherein the cellulose is unmodified cellulose.

21. An antimicrobial composition comprising a composite of claim 1.

22. The antimicrobial composition of claim 21, further comprising antimicrobial agent.

23. An ultraviolet protective coating comprising a composite of claim 1.

24. A dielectric material comprising a composite of claim 9.

25. A method of preparing a composite comprising lignin, cellulose and hemicellulose, wherein the cellulose content is about 40 to about 60% (w/w), the hemicellulose content is about 20 to about 40% (w/w), and the lignin content is about 10 to about 30% (w/w), wherein the lignin is selected from a kraft lignin or a lignosulfonate, wherein the hemicellulose is xvlan, and wherein the composite is transparent; comprising the steps of:
   a. dissolving the lignin and additional component in an ionic liquid to obtain a solution;
   b. applying the solution to a surface and obtaining a hydrogel; and
   c. drying the hydrogel to obtain the composite.

26. The method of claim 25, further comprising the step of removing the composite from the surface.

27. The method of claim 25, wherein the lignin and additional component are dissolved at a temperature from about 80 to about 100° C.

28. The method of claim 25, wherein the ionic liquid comprises a 1-alkyl-3-methylimidazolium salt.

29. The method of claim 25, wherein the ionic liquid comprises an allylimidazolium salt.

30. The method of claim 25, wherein the ionic liquid is selected from the group consisting of 1-ethyl-3-methylimidazolium acetate ([Emim][Ac]) and 1-allyl-3-methylimidazolim chloride, 1-butyl-3-methylimidazolium, or a combination thereof.

31. The method of claim 25, wherein the hydrogel is washed to remove at least some of the ionic liquid.

32. The method of claim 31, wherein the ionic liquid is reused after removal of water.

33. The method of claim 25, wherein the hydrogel is dried in a low humidity environment.

34. The method of claim 25, wherein the hydrogel is dried under a vacuum.

* * * * *